(12) United States Patent
Harris

(10) Patent No.: US 11,857,764 B2
(45) Date of Patent: Jan. 2, 2024

(54) AUTOMATIC DETECTION OF UN-BOLUSED MEALS

(71) Applicant: Tandem Diabetes Care, Inc., San Diego, CA (US)

(72) Inventor: Paul Harris, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 288 days.

(21) Appl. No.: 17/468,873

(22) Filed: Sep. 8, 2021

(65) Prior Publication Data

US 2021/0402091 A1    Dec. 30, 2021

Related U.S. Application Data

(63) Continuation of application No. 16/423,675, filed on May 28, 2019, now Pat. No. 11,116,901.

(60) Provisional application No. 62/677,433, filed on May 29, 2018.

(51) Int. Cl.
*A61M 5/172* (2006.01)
*A61M 5/142* (2006.01)
*A61M 5/14* (2006.01)

(52) U.S. Cl.
CPC ...... *A61M 5/1723* (2013.01); *A61M 5/14244* (2013.01); *A61M 5/1413* (2013.01); *A61M 2005/14208* (2013.01); *A61M 2005/14268* (2013.01); *A61M 2205/52* (2013.01)

(58) Field of Classification Search
None
See application file for complete search history.

(56) References Cited

U.S. PATENT DOCUMENTS 10,792,423 B2 * 10/2020 Chen .................. A61M 5/1723

* cited by examiner

*Primary Examiner* — Manuel A Mendez
(74) *Attorney, Agent, or Firm* — Morgan, Lewis & Bockius LLP

(57) ABSTRACT

Missed meal bolus reminders or alerts require a user to access the user's pump and/or remote control to clear the reminder/alert even when the user skipped a meal such that no meal bolus was needed. CGM data can be leveraged such that the missed meal bolus alert is only triggered when glucose levels rise in response to consuming the meal within the programmed time window. Therefore, the alert is only provided when a meal is actually consumed and no bolus has been delivered. This further allows the user to be alerted sooner, i.e., as soon as glucose levels rise a predetermined amount or passed a predetermined threshold indicating consumption of a meal as opposed to only at the end of the programmed window.

20 Claims, 5 Drawing Sheets

AUTOMATIC DETECTION OF UN-BOLUSED MEALS

RELATED APPLICATIONS

This application is a continuation of U.S. application Ser. No. 16/423,675 filed May 28, 2019, which claims the benefit of U.S. Provisional Application No. 62/677,433 filed May 29, 2018, each of which is hereby incorporated herein in its entirety by reference.

TECHNICAL FIELD

The present invention is directed to portable infusion pumps and more particularly programming for portable infusion pumps.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of insulin injecting pumps that have been developed for the administration of insulin for those suffering from both type I and type II diabetes. Some insulin injecting pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Such pumps can also deliver medicaments other than or in addition to insulin, such as glucagon, pramlintide, etc. Examples of such pumps and various features that can be associated with such pumps include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790, U.S. Pat. No. 8,287,495 and U.S. patent application Ser. No. 15/158,125, each of which is hereby incorporated herein by reference in its entirety.

Portable infusion pumps for delivering insulin or other medicaments can be used in conjunction with blood glucose monitoring systems, such as blood glucose meters (BGMs) and continuous glucose monitoring devices (CGMs). A CGM provides a substantially continuous estimated blood glucose level through a transcutaneous sensor that estimates blood analyte levels, such as blood glucose levels, via interrogation of the patient's interstitial fluid rather than the patient's blood. CGM systems typically consist of a transcutaneously-placed sensor, a transmitter and a monitor.

Ambulatory infusion pumps typically allow the patient or caregiver to adjust the amount of insulin or other medicament delivered, by a basal rate or a bolus, based on blood glucose data obtained by a BGM or a CGM, and in some cases include the capability to automatically adjust such medicament delivery. Some ambulatory infusion pumps may include the capability to interface with a BGM or CGM such as, e.g., by receiving measured or estimated blood glucose levels and automatically adjusting or prompting the user to adjust the level of medicament being administered or planned for administration or, in cases of abnormally low blood glucose readings, reducing or automatically temporarily ceasing or prompting the user temporarily to cease or reduce insulin administration. These portable pumps may incorporate a BGM or CGM within the hardware of the pump or may communicate with a dedicated BGM or CGM via wired or wireless data communication protocols, directly and/or via a device such as a smartphone. One example of integration of infusion pumps with CGM devices is described in U.S. Patent Publication No. 2014/0276419, which is hereby incorporated by reference herein.

SUMMARY OF THE INVENTION

Missed meal bolus reminders or alerts require a user to access the user's pump and/or remote control to clear the reminder/alert even when the user skipped a meal such that no meal bolus was needed. CGM data can be leveraged such that the missed meal bolus alert is only triggered when glucose levels rise in response to consuming the meal within the programmed time window. Therefore, the alert is only provided when a meal is actually consumed and no bolus has been delivered. This further allows the user to be alerted sooner, i.e., as soon as glucose levels rise a predetermined amount or passed a predetermined threshold indicating consumption of a meal as opposed to only at the end of the programmed window.

In an embodiment, an ambulatory infusion pump system can include a pump mechanism configured to facilitate delivery of a medicament to a patient, a memory adapted to store parameters relating to delivery of the medicament, a communications device adapted to receive information from a continuous glucose monitoring system and a processor functionally linked to the pump mechanism, the memory and the communications device. The processor can be configured to store in the memory a missed meal bolus alarm defining a time period during which a meal is expected to be consumed and provide a reminder to the user to deliver a meal bolus if no meal bolus is delivered by the pump mechanism during the time period. At the beginning of the time period, the processor can monitor CGM data for the user from the continuous glucose monitoring system and compare the CGM data to a threshold relating to glucose levels. The processor can provide the reminder to the user to deliver the meal bolus only if the CGM data exceeds the threshold (indicating consumption of a meal) and no meal bolus has been delivered by the pump mechanism.

In an embodiment, an ambulatory infusion pump system can include a pump mechanism configured to facilitate delivery of a medicament to a patient, a memory adapted to store parameters relating to delivery of the medicament, a communications device adapted to receive information from a continuous glucose monitoring system and a processor functionally linked to the pump mechanism, the memory and the communications device. The processor can be configured to store in the memory a missed meal bolus alarm defining a time period during which a meal is expected to be consumed and provide a reminder to the user to deliver a meal bolus if no meal bolus is delivered by the pump mechanism during the time period. The processor can further determine whether or not a meal was consumed by the user during the time period. If the processor determines that no meal was consumed by the user during the time period, the processor can cancel the missed meal bolus alarm at the end of the time period.

BRIEF DESCRIPTION OF THE DRAWINGS

Subject matter hereof may be more completely understood in consideration of the following detailed description of various embodiments in connection with the accompanying figures, in which.

Figure 1:
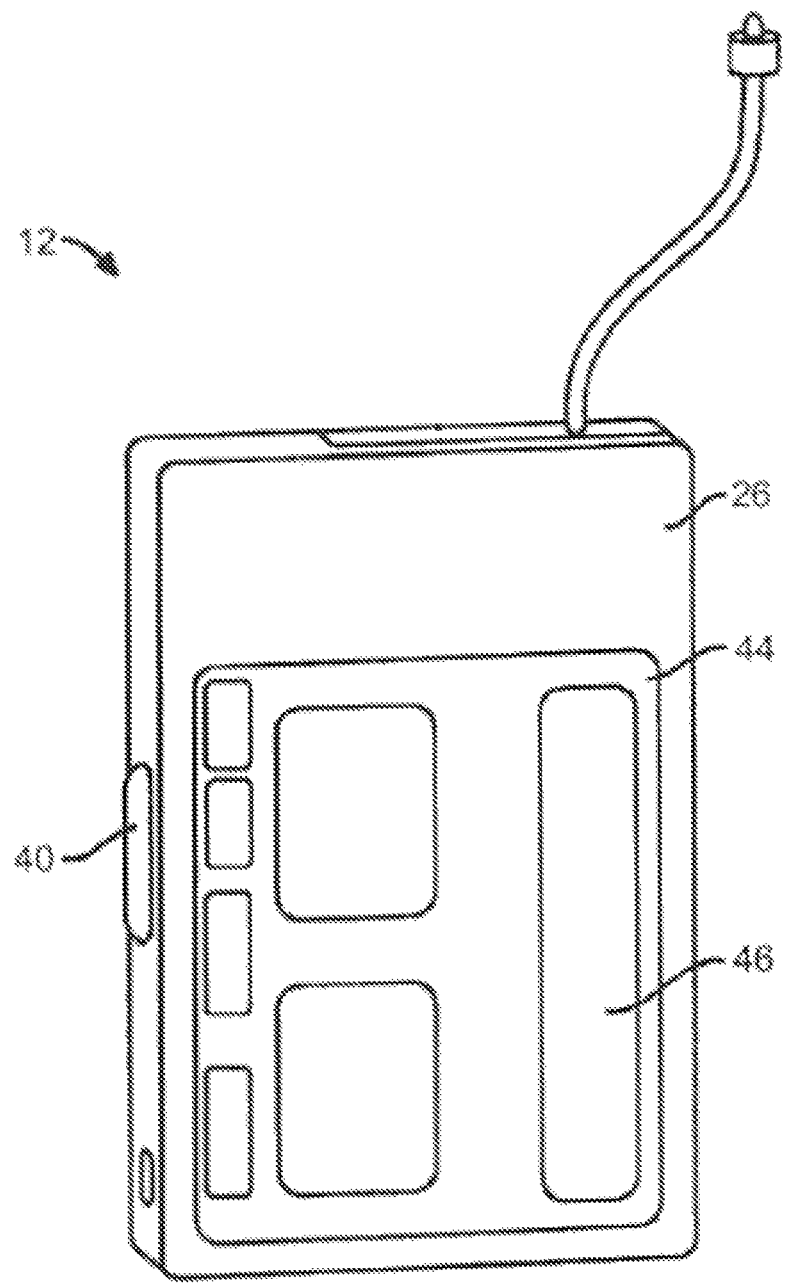
FIG. 1 is a medical device that can be used with embodiments of the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an embodiment of a medical device according to the disclosure. In this embodiment, the medical device is configured as a pump 12, such as an infusion pump, that can include a pumping or delivery mechanism and reservoir for delivering medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be a portable insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient. In a further embodiment, the medical device can be a glucose meter such as a BGM or CGM.

Figure 2:
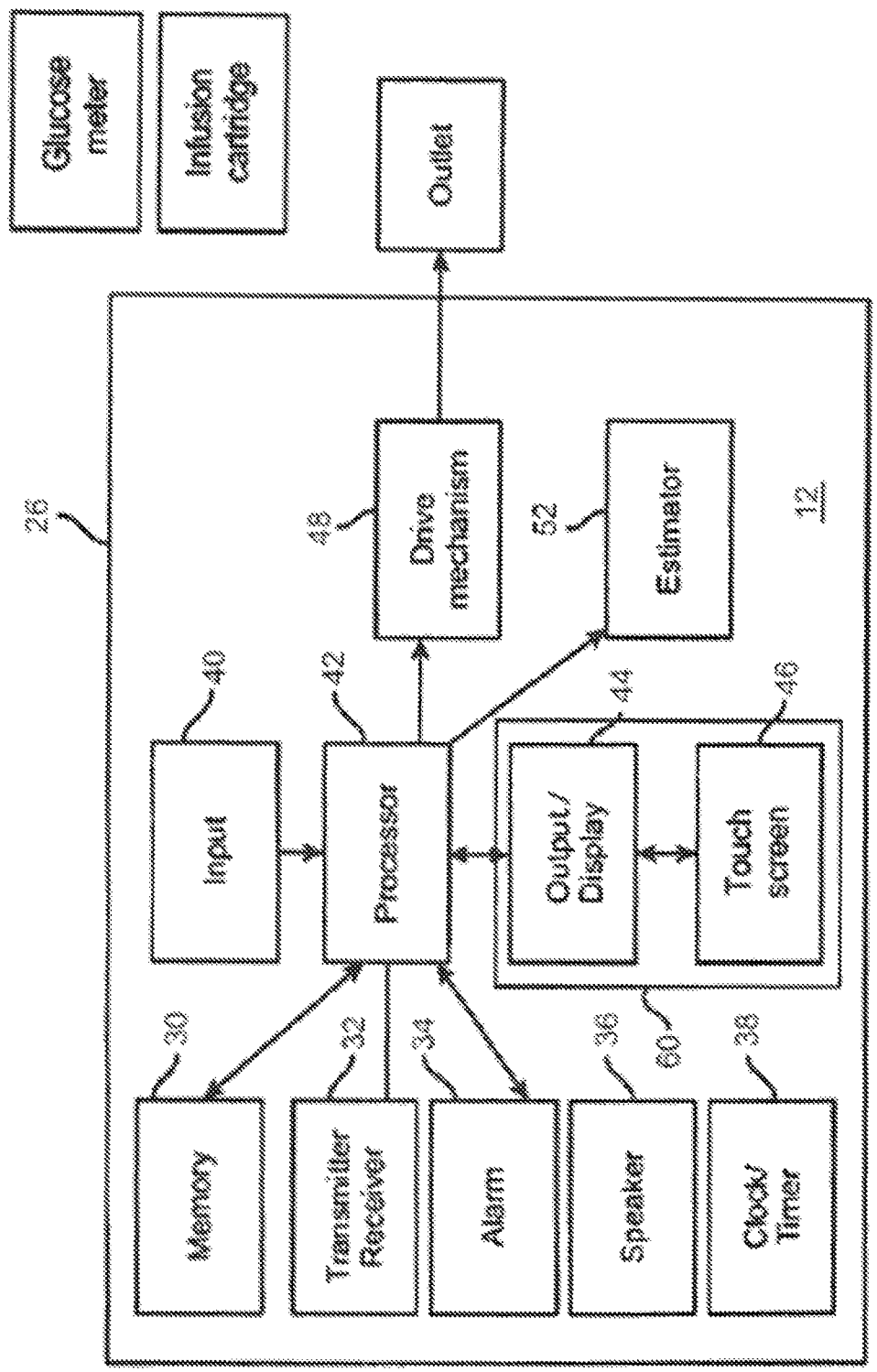
FIG. 2 is a block diagram representing a medical device that can be used with embodiments of the disclosure.

FIG. 2 illustrates a block diagram of some of the features that can be used with embodiments of the present invention, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figure 3:
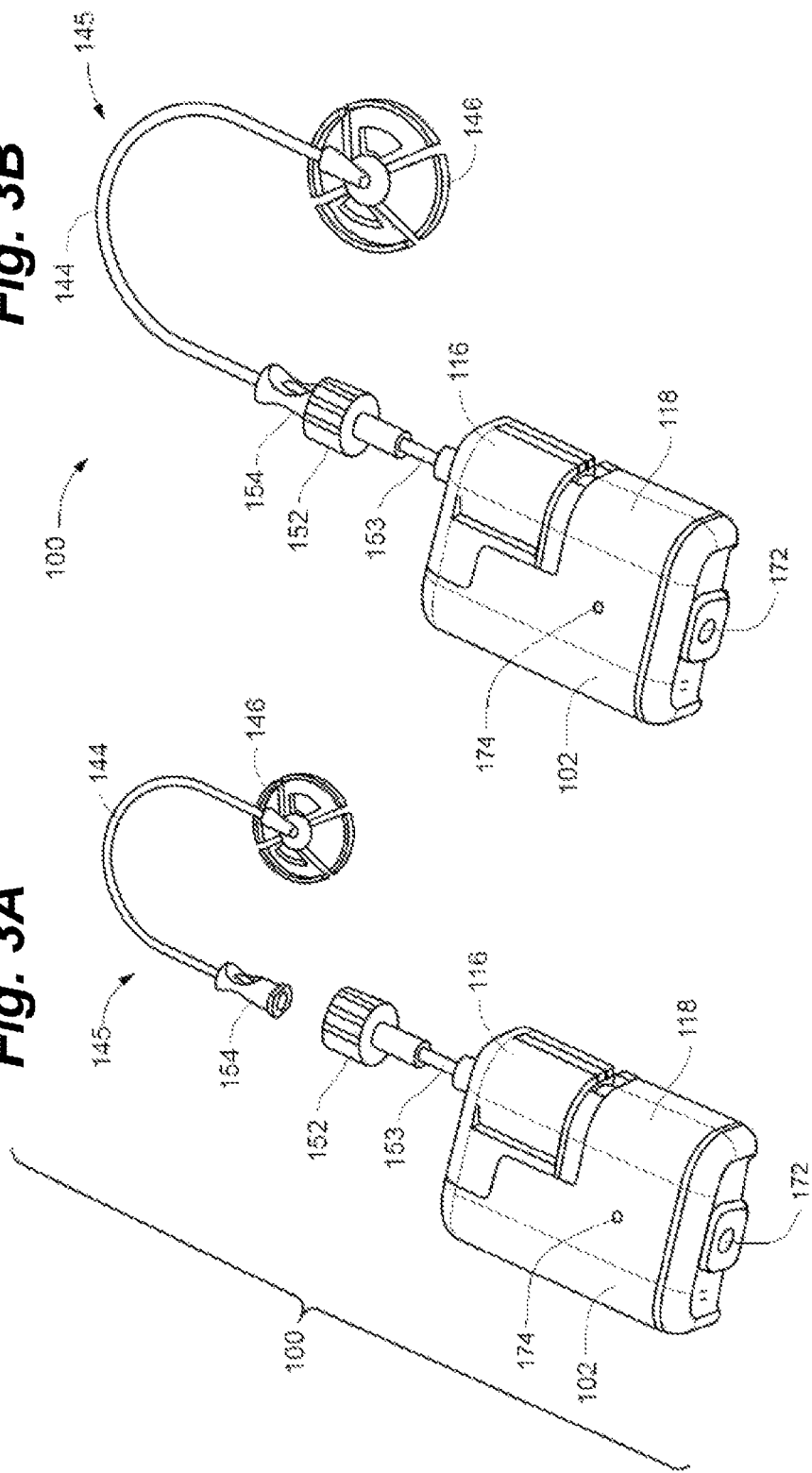
FIGS. 3A-3B depict an embodiment of a pump system according to the disclosure.

FIGS. 3A-3B depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118. Pump system 100 can further include an infusion set 145 having a connector 154 that connects to a connector 152 attached to pump 102 with tubing 153. Tubing 144 extends to a site connector 146 that can attach or be pre-connected to a cannula and/or infusion needle that punctures the patient's skin at the infusion site to deliver medicament from the pump 102 to the patient via infusion set 145.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
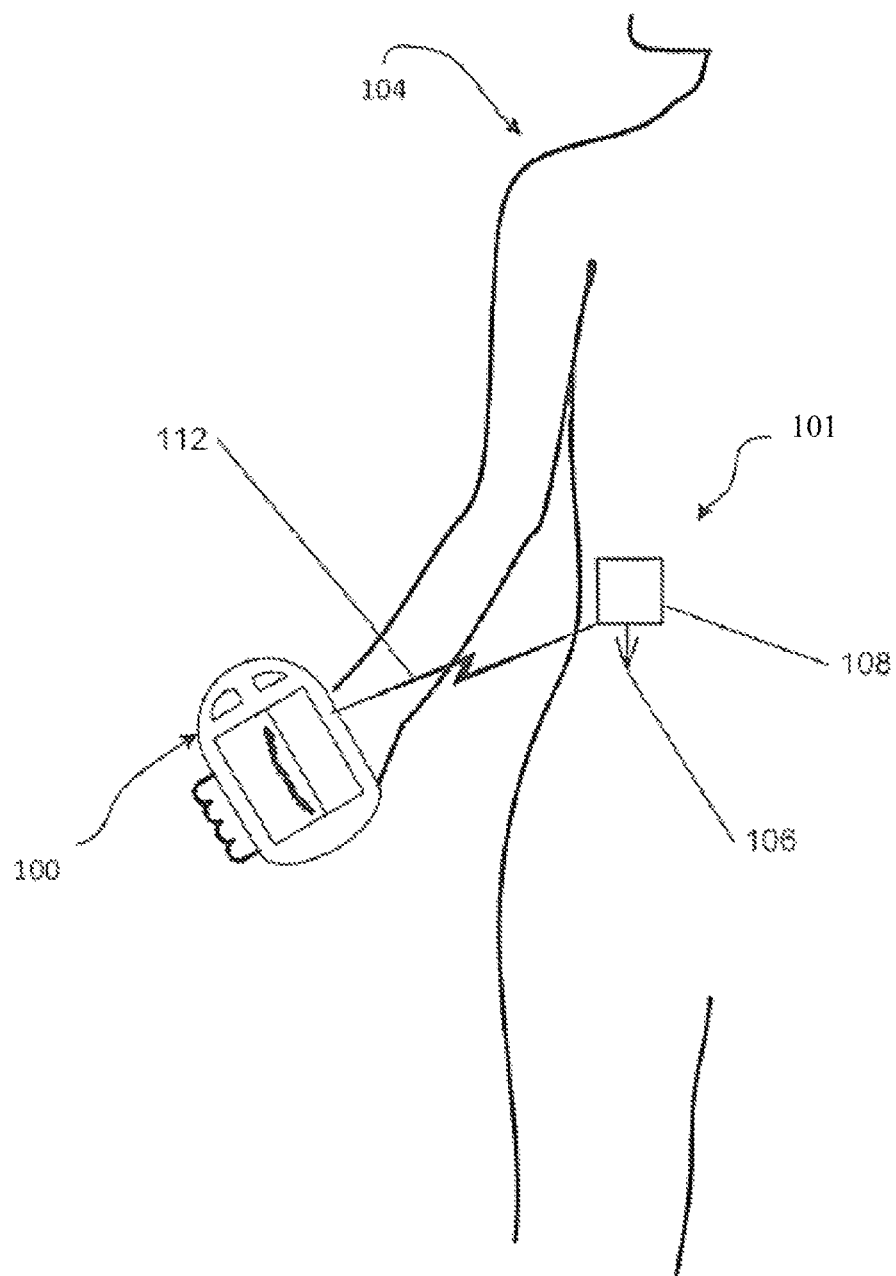
FIG. 4 is a schematic representation of a system according to the disclosure.

Pump 12 or 102 can interface directly or indirectly (via, e.g., a smartphone or other device) with a glucose meter, such as a blood glucose meter (BGM) or a continuous glucose monitor (CGM). Referring to FIG. 4, an exemplary CGM system 100 according to an embodiment of the present invention is shown (other CGM systems can be used). The illustrated CGM system includes a sensor 101 affixed to a patient 104 that can be associated with the insulin infusion device in a CGM-pump system. The sensor 101 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be associated with the patient's blood glucose (BG) level. The sensor 101 includes a sensor body 108 that transmits data associated with the interstitial fluid to which the sensor probe 106 is exposed. The data may be transmitted from the sensor 101 to the glucose monitoring system receiver 100 via a wireless transmitter, such as a near field communication (NFC) radio frequency (RF) transmitter or a transmitter operating according to a "Wi-Fi" or Bluetooth® protocol, Bluetooth® low energy protocol or the like, or the data may be transmitted via a wire connector from the sensor 101 to the monitoring system 100. Transmission of sensor data to the glucose monitoring system receiver by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In an embodiment of a pump-CGM system having a pump 12, 102 that communicates with a CGM and that integrates CGM data and pump data as described herein, the CGM can automatically transmit the glucose data to the pump. The pump can then automatically determine therapy parameters and deliver medicament based on the data. Such an automatic pump-CGM system for insulin delivery can be referred to as an artificial pancreas system that provides closed-loop therapy to the patient to approximate or even mimic the natural functions of a healthy pancreas. In such a system, insulin doses are calculated based on the CGM readings (that may or may not be automatically transmitted to the pump) and are automatically delivered to the patient at least in part based on the CGM reading(s).

For example, if the CGM indicates that the user has a high blood glucose level or hyperglycemia, the system can automatically calculate an insulin dose necessary to reduce the user's blood glucose level below a threshold level or to a target level and automatically deliver the dose. Alternatively, the system can automatically suggest a change in therapy upon receiving the CGM data such as an increased insulin basal rate or delivery of a bolus, but can require the user to accept the suggested change prior to delivery rather than automatically delivering the therapy adjustments.

If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the user, e.g., ingest carbohydrates and/or take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, that lowers blood glucose levels and a second medicament, e.g., glucagon, that raises blood glucose levels.

As with other parameters related to therapy, such thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

As is known in the art, a meal bolus alarm is an alarm that reminds the user to deliver a meal bolus during a predetermined time interval. For example, if the user typically eats breakfast between 7:00 am and 8:00 am, the user may set a missed meal bolus alarm/reminder for an interval between, e.g., 6:15 am and 8:00 am. In this example, an alarm sounds if a meal bolus is not delivered within this interval. Generally, the user can navigate the menu structure of an infusion pump and/or remote control for an infusion pump to a Missed Meal Bolus Reminder or Alarm setting. From there, the user can select a start time and an end time defining a period of time during which a meal is expected to be consumed for a reminder that is then stored in memory and can be turned on and off and/or set to be active on certain days. If the reminder or alarm is turned on and/or active on a given day, the pump and/or remote will detect whether or not a meal bolus was programmed and/or delivered during the programmed period of time. If a meal bolus is delivered, then the pump takes no further action. However, if no meal bolus is delivered by the programmed end time, the pump will automatically issue a missed meal bolus alarm reminder or alert to remind the user to deliver a meal bolus responsive to the expected meal. Further details regarding missed meal bolus alarms/reminders can be found in U.S. Pat. No. 8,690,856, which is hereby incorporated by reference herein in its entirety.

Existing infusion pumps therefore can be programmed to alert the user if no bolus is given during a specified time window, but do so automatically if no bolus is delivered without detecting if the patient actually ate a meal such that the bolus is actually required. For example, a user may at times skip a usual meal for which a missed bolus alarm or reminder is programmed such that the alarm/reminder is not necessary. With missed meal bolus reminders or alerts as described above, the reminder/alert requiring the user to access the user's pump and/or remote control and clear the reminder/alert even when the user skipped a meal is an unnecessary hassle. Embodiments described herein seek to address this issue by leveraging CGM data such that the missed meal bolus alert is only triggered when glucose levels rise in response to consuming the meal within the programmed time window. Therefore, the alert is only provided when a meal is actually consumed and no bolus has been delivered. This further allows the user to be alerted sooner, i.e., as soon as glucose levels rise a predetermined amount or passed a predetermined threshold indicating consumption of a meal as opposed to only at the end of the programmed window.

In one embodiment, software resident on the pump and/or a device for remotely controlling the pump reads and/or records the glucose level/status from the CGM at the start of the programmed meal window. During the meal window, the software continuously or periodically checks if the glucose level has risen by more than a certain threshold above the starting level. The threshold can be, for example, an amount above the starting level, a percentage above the starting level and/or a predetermined high glucose level threshold. In various embodiments, the detection threshold could be fixed, selected from a limited list of options, or completely user specified.

The software alerts with a missed bolus alarm/reminder only if the glucose level has risen above the threshold and no bolus has been administered during the meal window. In various embodiments, the software can provide the alert when the threshold is reached before the end of the programmed time period or can be delayed until the end of the time period even after reaching the threshold in order to enable to user to still deliver the bolus within the programmed window. If the threshold has not been reached by the end of the programmed missed meal bolus window, the missed meal bolus alert/reminder is not provided to the user. This effectively provides an automatic cancellation of the missed meal bolus alarm based on the CGM data indicating no meal was consumed, which saves the user the inconvenience of having to address an unneeded alert.

In various embodiments, the software can utilize other statistical measures alternatively and/or in addition to glucose level. For example, the software can analyze the glucose rate (e.g., in mg/dL/min) during the meal window and alert only when the glucose rate is above a threshold and/or analyze the change in glucose rate during the meal window and alert only when the glucose rate changes by a threshold.

Figure 5:
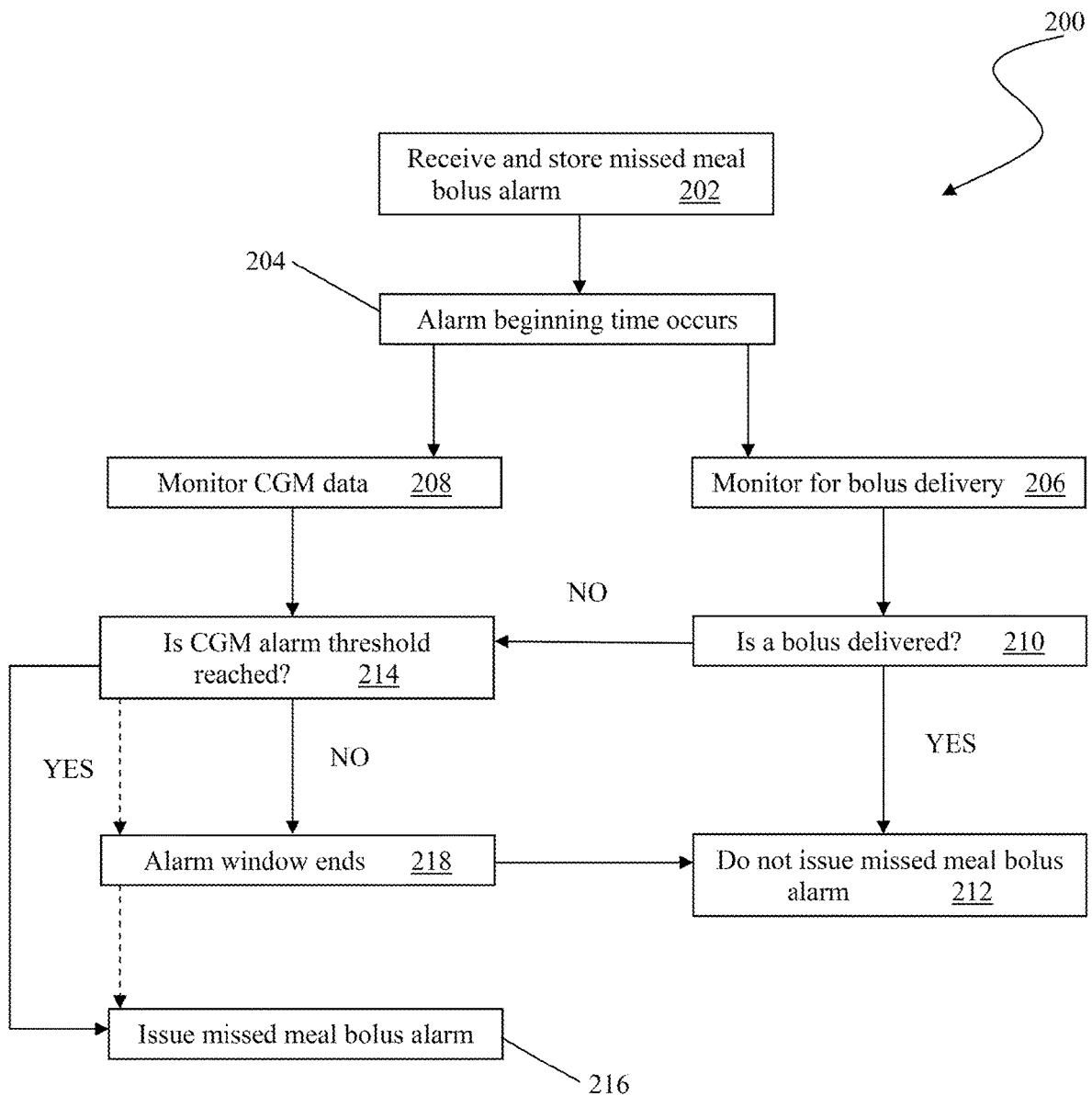
FIG. 5 depicts an embodiment of a method of providing diabetes therapy according to an embodiment.

FIG. 5 depicts an embodiment of a method 200 of providing diabetes therapy that includes detecting un-bolused meals and modifying missed meal bolus alarms according to an embodiment. At step 202 programming for a missed meal bolus alarm for an infusion pump is received and stored. In embodiments, the alarm input can be received via a user interface of and stored via a memory of the infusion pump, a remote control device, etc. The method continues at step 204 when the beginning time for the programmed alarm is reached on a day for which the programmed alarm is turned on/active.

During the programmed time window, the system monitors both whether or not a meal bolus is delivered with the pump at step 206 and the CGM data for the user at step 208. At step 210, the system determines if a meal bolus has been delivered with the pump. If so, at step 212 the missed meal bolus alarm is cancelled and no alarm is issued because a bolus corresponding to the scheduled meal was delivered. When no meal bolus has been delivered, the system at step 214 continually monitors the CGM data to determine if the CGM alarm threshold has been reached. If the CGM alarm threshold is reached and no meal bolus has been delivered, the missed meal bolus alarm is issued at step 216. This can be done, for example, at the time the threshold is reached as indicated by the solid arrow in FIG. 5 or only after the programmed end time of the alarm window is reached at step 218 without a meal bolus being delivered as indicated by the dashed arrows in FIG. 5. If the CGM alarm threshold is not reached when the alarm window ends at step 218, the system reverts to step 212 and no missed meal bolus alarm is issued because the system has determined from the CGM data that no meal was consumed. As noted above, method 200 saves a user from the hassle and inconvenience of responding to unnecessary missed meal bolus alarms when no meal was consumed during a programmed meal window.

In embodiments, the software can further automatically disable the missed meal bolus reminder if the glucose level goes below a low threshold and/or is dropping at a rate greater than a threshold. For example, if a user's glucose level is low, the carbohydrates consumed during the meal window may be needed to bring the user's glucose level up to a safer level and delivery of a meal bolus may drop the user's glucose level to a dangerously low level. By disabling the bolus reminder when a user's glucose level is below a certain predetermined threshold, delivery of such an unneeded bolus can be deterred.

Although primarily described herein with respect to a processor of an infusion pump in communication with a CGM, it should be understood that some or all of the steps of the methods described herein can be performed by a processor of a remote control device including, for example, a consumer electronic device such as a smartphone or a dedicated remote controller, in communication with a CGM. For example, the remote control device may receive and store the missed meal bolus alarm, communicate with the CGM to receive CGM data and determine whether or not the missed meal bolus alarm should be issued. Such remote control device may communicate with the pump to determine if a bolus was delivered with the pump and/or the device may inherently know whether or not a bolus has been delivered by receiving the bolus programming at the remote control device and issuing an operating command to the pump to deliver the bolus.

Although the embodiments herein are specifically described with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106 and 10,279,107. commonly owned U.S. Patent Publication Nos. 2009/0287180; 2012/0123230; 2013/0053816; 2014/0276419; 2014/0276420; 2014/0276423; 2014/0276569; 2014/0276570; 2016/0082188; 2017/0142658; 2017/0182248; 2017/0250971; 2018/0021514; 2018/0071454 and 2018/0193555 commonly owned U.S. patent application Ser. Nos. 16/266,471 and 16/380,475.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. A method of diabetes therapy, comprising:
   causing delivery of a medicament to a user with an ambulatory infusion pump;
   receiving CGM data from a continuous glucose monitoring system;
   receiving input from a user relating to a timing of an expected meal to be consumed by the user;
   monitoring the CGM data for the user from the continuous glucose monitoring system based on the timing of the expected meal;
   comparing the CGM data to a threshold relating to glucose levels; and
   providing a reminder to deliver a meal bolus for the expected meal if the CGM data exceeds the threshold and no meal bolus has been delivered by the ambulatory infusion pump for the expected meal.

2. The method of claim 1, wherein providing the reminder to deliver the meal bolus occurs at a time when the CGM data is determined to exceed the threshold if no meal bolus has been delivered by the ambulatory infusion pump during the time period.

3. The method of claim 1, further comprising not providing the reminder if the CGM data does not exceed the threshold during the time period.

4. The method of claim 1, further comprising not providing the reminder if a meal bolus is delivered with ambulatory infusion pump for the expected meal.

5. The method of claim 1, wherein comparing the CGM data to the threshold includes comparing glucose levels to the threshold.

6. The method of claim 5, wherein the threshold is a predetermined glucose level amount greater than a glucose level at the time the input relating to the timing of the expected meal was received.

7. The method of claim 5, wherein the threshold is a predetermined percentage increase of glucose level greater than a glucose level at the time the input relating to the timing of the expected meal was received.

8. The method of claim 5, wherein the threshold is a predetermined high glucose level.

9. The method of claim 1, wherein comparing the CGM data to the threshold includes comparing glucose level rate of change to the threshold.

10. The method of claim 1, wherein providing the reminder to deliver the meal bolus includes providing the reminder on a user interface of the ambulatory infusion pump.

11. The method of claim 1, wherein providing the reminder to deliver the meal bolus includes providing the reminder with a remote control device configured to remotely control the ambulatory infusion pump.

12. The method of claim 1, wherein receiving input from a user relating to a timing of an expected meal to be consumed by the user includes receiving programming for a missed meal bolus alarm defining a time period during which a meal is expected to be consumed.

13. A method of diabetes therapy, comprising:
    causing delivery of a medicament to a user with an ambulatory infusion pump;
    receiving CGM data from a continuous glucose monitoring system;
    receiving input from a user relating to a timing of an expected meal to be consumed by the user;
    determining whether the expected meal was consumed by the user; and
    providing a reminder to deliver a meal bolus for the expected meal if it is determined that the expected meal was consumed by the user and no meal bolus has been delivered by the ambulatory infusion pump for the expected meal.

14. The method of claim 13, wherein determining whether or not a meal was consumed by the user is based on the CGM data from the continuous glucose monitoring system.

15. The method of claim 14, wherein determining whether or not a meal was consumed by the user includes:
    monitoring the CGM data for the user from the continuous glucose monitoring system based on the timing of the expected meal; and
    comparing the CGM data to a threshold relating to glucose levels.

16. The method of claim 15, wherein comparing the CGM data to the threshold includes comparing glucose levels to the threshold.

17. The method of claim 16, wherein the threshold is selected from the group consisting of: a predetermined glucose level amount greater than a glucose level at the time the input relating to the timing of the expected meal was received, a predetermined percentage increase of glucose level greater than a glucose level at the time the input relating to the timing of the expected meal was received, and a predetermined high glucose level.

18. The method of claim 15, wherein comparing the CGM data to the threshold includes comparing glucose rate of change to the threshold.

19. The method of claim 13, wherein providing the reminder to deliver the meal bolus includes providing the reminder on a user interface of the ambulatory infusion pump.

20. The method of claim 13, wherein providing the reminder to deliver the meal bolus includes providing the reminder on a remote control device configured to remotely control and ambulatory infusion pump including the pump mechanism.

* * * * *